(12) United States Patent
Koyama

(10) Patent No.: US 10,942,348 B2
(45) Date of Patent: Mar. 9, 2021

(54) ENDOSCOPE OBJECTIVE OPTICAL SYSTEM

(71) Applicant: OLYMPUS CORPORATION, Hachioji (JP)

(72) Inventor: Yutaka Koyama, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 233 days.

(21) Appl. No.: 16/232,682

(22) Filed: Dec. 26, 2018

(65) Prior Publication Data

US 2019/0142249 A1 May 16, 2019

Related U.S. Application Data

(63) Continuation of application No. PCT/JP2017/024801, filed on Jul. 6, 2017.

(30) Foreign Application Priority Data

Sep. 28, 2016 (JP) .............................. JP2016-190281

(51) Int. Cl.
G02B 23/24 (2006.01)
A61B 1/00 (2006.01)
(Continued)

(52) U.S. Cl.
CPC ........ *G02B 23/243* (2013.01); *A61B 1/00096* (2013.01); *A61B 1/00174* (2013.01);
(Continued)

(58) Field of Classification Search
CPC ...... G02B 23/246; G02B 9/18; G02B 13/006; G02B 9/60; G02B 9/00; G02B 9/34;
(Continued)

(56) References Cited

U.S. PATENT DOCUMENTS 6,327,101 B1 12/2001 Miyano
7,796,342 B2 9/2010 Baba
(Continued)

FOREIGN PATENT DOCUMENTS

CN 104919353 A 9/2015
JP 2000330015 A 11/2000
(Continued)

OTHER PUBLICATIONS

Chinese Office Action (and English language translation thereof) dated Jul. 17, 2020 issued in counterpart Chinese Patent Application No. 201780041707.9.
(Continued)

*Primary Examiner* — Kristina M Deherrera
(74) *Attorney, Agent, or Firm* — Holtz, Holtz & Volek PC

(57) ABSTRACT

An endoscope objective optical system consists of in order from an object side, a front group having a negative refractive power, an aperture stop, and a rear group having a positive refractive power, wherein either the front group or the rear group includes one or more than one cemented lens, and the cemented lens includes a lens having a positive refractive power and a lens having a negative refractive power, and the rear group includes a positive lens which is a single lens, on the object side, and the following conditional expressions (1), (2), (3), and (4) are satisfied.

$$1.1 < Ih/ft < 1.8 \quad (1)$$

$$-ff/ft < 0.9 \quad (2)$$

$$45 < vd1 \quad (3)$$

$$LOs/Ih < 1.5 \quad (4)$$

where, Ih denotes the maximum image height, ft denotes a focal length of an overall endoscope objective optical
(Continued)

system, ff denotes a focal length of the front group, vd1 denotes Abbe's number for a glass material of the lens having a positive refractive power, on the object side of the rear group, and LOs denotes a distance from a first surface on the object side of the endoscope objective optical system up to the aperture stop, and here the first surface on the object side of the endoscope objective optical system is a lens surface positioned nearest to object in the endoscope objective optical system.

5 Claims, 4 Drawing Sheets

(51) Int. Cl.
| | |
|---|---|
| *G02B 13/00* | (2006.01) |
| *A61B 1/05* | (2006.01) |
| *G02B 13/04* | (2006.01) |
| *A61B 1/307* | (2006.01) |
| *G02B 9/00* | (2006.01) |
| *G02B 9/60* | (2006.01) |
| *G02B 9/18* | (2006.01) |
| *A61B 1/06* | (2006.01) |
| *G02B 9/34* | (2006.01) |

(52) U.S. Cl.
CPC .............. *A61B 1/051* (2013.01); *A61B 1/307* (2013.01); *G02B 9/00* (2013.01); *G02B 9/18* (2013.01); *G02B 9/60* (2013.01); *G02B 13/006* (2013.01); *G02B 13/04* (2013.01); *A61B 1/00009* (2013.01); *A61B 1/00186* (2013.01); *A61B 1/0676* (2013.01); *G02B 9/34* (2013.01)

(58) Field of Classification Search
CPC ..... G02B 13/04; A61B 1/00096; A61B 1/307; A61B 1/00174; A61B 1/051; A61B 1/0016; A61B 1/0676; A61B 1/00009
USPC ......................................................... 359/756
See application file for complete search history.

(56) References Cited

U.S. PATENT DOCUMENTS

| | | | |
|---|---|---|---|
| 8,243,129 | B2 | 8/2012 | Uzawa |
| 8,331,041 | B2 | 12/2012 | Katakura et al. |
| 9,140,888 | B2 | 9/2015 | Fujii |
| 9,622,652 | B2 | 4/2017 | Igarashi |
| 2012/0057251 | A1 | 3/2012 | Takato |
| 2015/0309289 | A1 | 10/2015 | Nakamura |

FOREIGN PATENT DOCUMENTS

| | | |
|---|---|---|
| JP | 2009136387 A | 6/2009 |
| WO | 2011070897 A1 | 6/2011 |
| WO | 2011070930 A1 | 6/2011 |
| WO | 2011148822 A1 | 12/2011 |
| WO | 2011152099 A1 | 12/2011 |
| WO | 2014175038 A1 | 10/2014 |
| WO | 2014208373 A1 | 12/2014 |

OTHER PUBLICATIONS

International Preliminary Report on Patentabiliy (IPRP) (and English language translation thereof) and Written Opinion dated Apr. 11, 2019 issued incounterpart International Application No. PCT/JP2017/024801.
International Search Report (ISR) dated Sep. 19, 2017 issued in International Application No. PCT/JP2017/024801.
Japanese Office Action dated Apr. 4, 2018 issued in counterpart Japanese Application No. 2018-502268.
Written Opinion dated Sep. 19, 2017 issued in International Application No. PCT/JP2017/024801.

SA  
FNO 5.191

AS  
IH 0.94

DT  
IH 0.94

CC  
IH 0.94

ENDOSCOPE OBJECTIVE OPTICAL SYSTEM

CROSS-REFERENCE TO RELATED APPLICATION

The present application is a continuation application of PCT/JP2017/024801 filed on Jul. 6, 2017 which is based upon and claims the benefit of priority from Japanese Patent Application No. 2016-190281 filed on Sep. 28, 2016; the entire contents of which are incorporated herein by reference.

BACKGROUND OF THE INVENTION

Field of the Invention

The present invention relates to an endoscope objective optical system, and mainly to an objective optical system of a medical endoscope

Description of the Related Art

As an endoscope intended for internal organs of urinary system, an endoscope in which an insertion portion is to be inserted transurethrally (hereinafter, appropriately referred to as 'endoscope for urinary organs') is available. In the endoscope for urinary organs, for making the insertion portion insertable into urethra, it is essential that an outer diameter of the insertion portion is not more than 7 mm. Therefore, the diameter of the endoscope for urinary organs is thinner than an insertion portion of an endoscope for alimentary tract which is widely known for medical examination of stomach and large intestine.

Furthermore, in a case of observing a narrow sac-like internal organ such as urinary bladder, a method of bending the insertion portion 90 degrees or more, and observing an inlet direction of the organ is adopted. In this case, when an overall length of an optical system is short, it is possible to shorten a length from a front end up to a bent portion of the endoscope. For this reason, an endoscope in which the overall length of the optical system is short is superior in value in observation of sac-like internal organs, as it enables observation of a wider range.

Moreover, the internal organs of urinary system are normally filled with urine. Therefore, an objective optical system to be used in the endoscope for urinary organs has an optical design envisaged for in-water observation.

In International Unexamined Patent Application Publication No. 2014/208373, an endoscope objective optical system in which an angle of view at the time of in-water observation (hereinafter, referred to as 'in-water angle of view) is wide has been disclosed. The endoscope objective optical system of International Unexamined Patent Application Publication No. 2014/208373 includes a first group having a negative refractive power, an aperture stop, and a second group having a positive refractive power. In the endoscope objective optical system of Patent Literature 1, the in-water angle of view is in the range of 105° to 164°.

Moreover, in International Unexamined Patent Application Publication No. 2014/208373, there is a description about a medium of an observation space. The observation space in this case is a space in a case of observing internal organs of urinary system by an endoscope for urinary organs. In International Unexamined Patent Application Publication No. 2014/208373, it has been indicated that the medium of the observation space in this case is a perfusion solution or urine of which water is a main constituent, and that it is reasonable to deem a refractive index of those media to be equivalent to a refractive index of water.

Furthermore, in International Unexamined Patent Application Publication No. 2014/208373, it has been pointed out that the in-water angle of view is narrowed with respect to an angle of view at the time observation in air (hereinafter, appropriately referred to as 'angle of view in air'). In Patent Literature 1, a relation of the angle of view in air and the in-water angle of view is shown as follows.

|  | Angle of view in air | | | |
|---|---|---|---|---|
|  | 180° | 160° | 140° | 120° |
| In-water angle of view | 97.2° | 95.3° | 89.7° | 81.0° |

The angle of view in air and in-water angle of view are calculated by letting a refractive index of water for a d-line (wavelength 587.6 nm) to be 1.333 and letting a lens nearest to object in the endoscope objective optical system to be flat.

The abovementioned relationship signifies that even when it is an endoscope objective optical system in which the angle of view in air is 120° for example, when this endoscope objective optical system is used in an endoscope for urinary bladder, the angle of view at the time of practical use, or in other words at the time of in-water observation, is narrowed to 81°. In International Unexamined Patent Application Publication No. 2014/208373, a fact that even with an endoscope objective optical system with a wide angle of view in air, it is not possible to explore a pathological lesion in an entire inner surface of a urinary bladder, has been addressed as an a problem.

Moreover, in International Unexamined Patent Application Publication No. 2011/152099, a super wide angle endoscope objective optical system has been disclosed. In the endoscope objective optical system of International Unexamined Patent Application Publication No. 2011/152099, the angle of view in air is 180° or more. The endoscope objective optical system of Patent Literature 2 consists of in order from an object side, a first group which includes in order from an object side a negative lens and a positive lens and a second group which includes in order from the object side, a positive lens and a cemented lens of a negative lens and a positive lens.

Moreover, in Japanese Patent Application Laid-open Publication No. 2009-136387, a wide angle objective optical system for capsule endoscope has been disclosed. In an example in Japanese Patent Application Laid-open Publication No. 2009-136387, an angle of view in air is 168°. When the abovementioned angle of view in air is converted to an in-water angle of view, the in-water angle of view is 96.5°. The endoscope objective optical system of Patent Literature 3 consists of in order from an object side five lenses including a negative meniscus lens, a positive meniscus lens, and a cemented lens.

Moreover, in International Unexamined Patent Application Publication No. 2011/148822, a super wide angle endoscope objective optical system has been disclosed. In the endoscope objective optical system of International Unexamined Patent Application Publication No. 2011/148822, the angle of view in air is 180° or more. The endoscope objective optical system of International Unexamined Patent Application Publication No. 2011/148822 consists of a first group having a negative refractive power, an aperture stop, and a second group having a positive refractive power.

Moreover, in an endoscope objective optical system disclosed in Patent Literature 5, there has been no description about the in-water angle of view. However, in all examples, since a front-end surface has a positive refractive power, an arrangement of the endoscope objective optical system of International Unexamined Patent Application Publication No. 2011/070897 is an arrangement which is advantageous for widening the in-water angle of view. For such reason, in the endoscope objective optical system of International Unexamined Patent Application Publication No. 2011/070897, an arrangement may be an arrangement that enables to achieve an adequately large in-water angle of view.

SUMMARY OF THE INVENTION

An endoscope objective optical system, consists of, in order from an object side:
a front group having a negative refractive power;
an aperture stop; and
a rear group having a positive refractive power, wherein
one of the front group and the rear group includes not less than one cemented lens, and
the cemented lens includes a lens having a positive refractive power and a lens having a negative refractive power, and
the rear group includes a single lens having a positive refractive power on the object side, and
the following conditional expressions (1), (2), (3), and (4) are satisfied.

$$1.1 < Ih/ft < 1.8 \quad (1)$$

$$-ff/ft < 0.9 \quad (2)$$

$$45 < vd1 \quad (3)$$

$$LOs/Ih < 1.5 \quad (4)$$

where,
Ih denotes the maximum image height in an in-water observation state,
ft denotes a focal length of an overall endoscope objective optical system,
ff denotes a focal length of the front group,
vd1 denotes Abbe's number for a glass material of the positive lens on the object side of the rear group, and
LOs denotes a distance from a first surface on the object side of the endoscope objective optical system up to the aperture stop, and here
the first surface on the object side of the endoscope objective optical system is a lens surface positioned nearest to object in the endoscope objective optical system.

DETAILED DESCRIPTION OF THE INVENTION

Figure 1A:
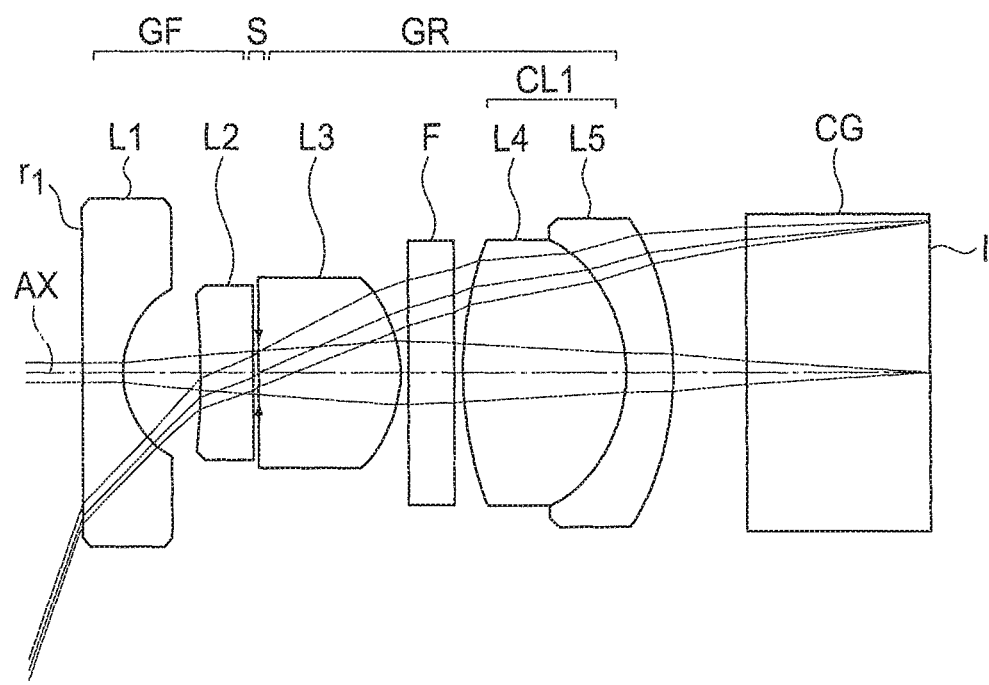
FIG. 1A is a lens cross-sectional view showing a basic arrangement of an endoscope objective optical system of a first embodiment.

Endoscope objective optical systems according to embodiments will be described below in detail by referring to the accompanying diagrams.
Reasons for and effects of adopting such arrangement for an endoscope objective optical system according to a first embodiment will be described below by using the diagrams. However, the present invention is not restricted to the endoscope objective optical systems according to the embodiments described below.
A basic arrangement of the endoscope objective optical system of the first embodiment will be described below. An optical system of the basic arrangement includes, in order from an object side, a front group GF having a negative refractive power, an aperture stop S, and a rear group GR having a positive refractive power, and either the front group GF or the rear group GR includes one or more than one cemented lenses CL1, and the rear group GR includes a third lens L3 which is a single lens having a positive refractive power, on the object side.
The endoscope objective optical system of the present embodiment is a super wide angle optical system. Therefore, for securing an extremely wide angle of view, a so-called retro-focus arrangement which is most appropriate for widening the angle of view has been adopted in the basic arrangement.
FIG. 1A is a lens cross-sectional arrangement view showing an example of the basic arrangement of the endoscope objective optical system of the present embodiment. In the basic arrangement, the optical system includes in order from the object side, the front group GF having a negative refractive power, the aperture stop S, and the rear group GR having a positive refractive power.
Furthermore, in the basic arrangement, the rear group GR includes the cemented lens CL1 which includes a fourth lens L4 having a positive refractive power and a fifth lens L5 having a negative refractive power. Accordingly, a chromatic aberration is corrected.
Furthermore, the rear group GR includes the third lens L3 which is a single lens having a positive refractive power, on the object side. For securing a wide angle of view at the time of in-water observation, it is necessary to let the front group GF to have a strong negative refractive power. For letting the overall optical system to have a positive refractive power, it is necessary to dispose a strong positive refractive power in the rear group GR. This is secured by the third lens L3 which is a single lens having a positive refractive power in the rear group GR. Preferably, it is desirable to dispose the third lens L3 having a positive refractive power nearest to object in the rear group GR. Moreover, in a case in which the abovementioned third lens L3 having a positive refractive power is disposed at a rear of the image side of the aperture stop S, sandwiching one or more than one lenses, and not immediately on the image side of the aperture stop S, a position through which an off-axis light ray passes is spaced apart from an optical axis AX, and an effective diameter of lens becomes large, and therefore it is not desirable. Therefore, an arrangement is let to be such that the third lens L3 at the rear of the image side of the aperture stop S is a single lens having a positive refractive power.

In such manner, the basic arrangement for the endoscope objective optical system of the present embodiment is an arrangement in which all of, the smalling of diameter (making an outer diameter of a lens small), widening of angle, and shortening of the overall length of the optical system are taken into consideration.

In super wide angle optical systems, there are optical systems in which a lens having a positive refractive power is disposed on the object side of an aperture stop. However, the positive refractive power disposed in the front group acts in a direction of narrowing the angle of view. Moreover, since the positive refractive power locates an entrance-pupil position more on the image side, the positive refractive power increases the lens outer diameter. Therefore, it is not desirable to dispose the lens having a positive refractive power on the object side of the aperture stop S.

In the present embodiment, the aperture stop S is disposed between the front group GF and the rear group GR. In a case in which a distance between the front group GF and the rear group GR is narrow, the aperture stop S may be provided to a lens surface. As a method of and an arrangement for providing the aperture stop S to a lens surface, a method and an arrangement in which a metallic light-shielding film is coated on the lens surface, and an opening portion is formed by etching, and a method and an arrangement in which a thin annular metal plate is pinched between a lens and a frame are available.

The rear group GR includes the third lens L3 having a positive refractive power and the cemented lens CL1. The cemented lens CL1 includes the fourth lens L4 having a positive refractive power and the fifth lens L5 having a negative refractive power. Moreover, an optical filter F is disposed in the rear group GR. In the present embodiment, the optical filter F is disposed between the third lens L3 having a positive refractive power and the cemented lens CL1.

The optical filter F is a filter such as an infra-red cut filter and a color-temperature conversion filter. These filters are used for sensitivity correction of an image pickup element such as a CCD (charge coupled device).

Moreover, a laser cut filter or a special function filter may be disposed in the optical system. As the laser cut filter, a filter for cutting-off laser light such as YAG (yttrium aluminum garnet) laser and semiconductor laser are available. As the special function filter, a notch filter which cuts a light ray of a specific wavelength band is available.

Moreover, for the optical filter F, an absorbing filter, a reflecting filter, and a combined filter in which the absorbing filter and the reflecting filer are combined may be used. Moreover, a filter having an anti-reflection film applied thereon may be used.

A glass block CG is disposed on the image side of the rear group GR. The glass block CG is intended to be a cover glass of a solid image pickup element. An image of an object having an image height Ih is formed on an image-side surface of the glass block CG. The image-side surface of the glass block CG coincides with an image pickup surface of the image pickup element.

Furthermore, the endoscope objective optical system according to the first embodiment will be described below.

The endoscope objective optical system according to the first embodiment is characterized by having the abovementioned basic arrangement and the following conditional expressions (1), (2), (3), and (4) are satisfied.

$$1.1 < Ih/ft < 1.8 \quad (1)$$

$$-ff/ft < 0.9 \quad (2)$$

$$45 < vd1 \quad (3)$$

$$LOs/Ih < 1.5 \quad (4)$$

where,

Ih denotes the maximum image height, ft denotes a focal length of an overall endoscope objective optical system, ff denotes a focal length of the front group GF, vd1 denotes Abbe's number for a glass material of the third lens having a positive refractive power on the object side of the rear group GF, and LOs denotes a distance from a first surface r1 on the object side of the endoscope objective optical system up to the aperture stop S, and here the first surface r1 on the object side of the endoscope objective optical system is a lens surface positioned nearest to object in the endoscope objective optical system.

Conditional expression (1) is a conditional expression related to the in-water angle of view. The maximum image height Ih is the maximum image height upon taking into consideration the in-water observation as well. Moreover, ft is the focal length of the overall endoscope objective optical system. However, in a case in which a first surface r1 on the object side has a curvature, the focal length varies in accordance with a refractive index of an object-side medium. Therefore, ft, similar to a definition of the focal length of a normal lens, is let to be a focal length when the object-side medium is let to be air.

In conditional expression (1), when a value of Ih/ft becomes small, the in-water angle of view becomes narrow, and when the value of Ih/ft becomes large, the in-water angle of view becomes wide.

In conventional endoscope objective optical systems designed for observation in air, an image height H is approximately proportional to sin of the focal length ft and an angle of incidence θa in many cases. Such endoscope objective optical systems have been known as objective optical systems of a so-called H=ft×sin θa type. Here, θa is an angle made by a principal light ray in an object-side medium space and an optical axis, and is an angle at the time of observation in air. In the objective optical system of H=ft×sin θa type, a value of H/ft is not more than 1.

Whereas in the endoscope objective optical system of the first embodiment, as revealed in conditional expression (1), the value of Ih/ft becomes more than 1. This signifies that in the endoscope objective optical system of the first embodiment, the maximum image height at the time of in-water observation is larger than the image height assumed at the time of observation in air. Exceeding a lower limit value of conditional expression (1) contributes to widening of the in-water angle of view. By a value falling below an upper limit value of conditional expression (1), it is possible to avoid an excessive widening of the in-water angle of view.

Conditional expression (2) is a conditional expression related to the negative refractive power of the front group GF. For achieving widening of the in-water angle of view, it is necessary to make the negative refractive power of the front group GF strong. At this time, the focal length of the front group (hereinafter, referred to as 'ff') becomes short. Here, ff being a negative value, '−ff' is standardized (normalized) by the focal length of the overall endoscope objective optical system, and an upper limit value is provided.

When an upper limit value of conditional expression (2) is exceeded, the in-water angle of view becomes narrow. In other words, it becomes difficult to achieve adequately the angle of view necessary for in-water observation.

Conditional expression (3) is a conditional expression related to a glass material of a lens having a positive refractive power in the rear group GR, which is nearest to object.

As mentioned above, for achieving the in-water angle of view, it is necessary to make the negative refractive power of the front group GF strong. For suppressing a spherical aberration which occurs in a lens having a strong negative refractive power, it is desirable to use a glass material of a high refractive index, and to make an arrangement such that a radius of curvature of the lens does not become excessively small.

However, an optical glass of a high refractive index that is procurable at present has a characteristic of having a high dispersion, or in other words, Abbe's number for the optical glass of a high refractive index is small. Therefore, for correcting a longitudinal chromatic aberration favorably, it is necessary to use a glass material with a low dispersion, or in other words, a glass material for which Abbe's number is large, for the fourth lens L4 having a positive refractive power in the rear group GR, in addition to the cemented lens CL1.

When a value falls below a lower limit value of conditional expression (3), it is not possible to correct the chromatic aberration of the optical system favorably. Or, two or more than two sets of cemented lenses are necessary, and the overall length of the optical system becomes long, and therefore it is not desirable.

Conditional expression (4) is a conditional expression related to the maximum diameter of a lens. In a wide angle lens, a case in which a so-called front-cell lens becomes a lens having the maximum diameter is common. In the endoscope objective optical system of the first embodiment, the lens having the first surface r1 on the object side, or in other words, the first lens L1 having a negative refractive power is equivalent to the front-cell lens.

In a super wide angle lens, an image ray height at the first lens L1 having a negative refractive power is almost determined by the angle of view and the entrance-pupil position. When the angle of view is determined, the entrance-pupil position becomes a parameter that determines the light-ray height at the first lens L1 having a negative refractive power. The farther away the entrance-pupil position toward the image side from the first surface r1 on the object side, the higher is the light-ray height at the first lens L1 having a negative refractive power. Therefore, for making small a diameter of the first lens L1 having a negative refractive power, it is necessary to devise an idea for bringing the entrance-pupil position closer to the first surface r1 on the object side.

For bringing the entrance-pupil position closer to the first surface r1 on the object side, a distance from the first surface r1 on the object side up to the aperture stop S (hereinafter, referred to as 'LOs') is to be made short. For this, LOs is standardized by the maximum image height Ih, and the upper limit value is provided.

When an upper limit value of conditional expression (4) is exceeded, the outer diameter of the first lens L1 having a negative refractive power becomes the maximum. With this, an endoscope, and particularly a front-end rigid portion becomes thick. Therefore, it is not desirable to exceed the upper limit value of conditional expression (4).

Next, reasons for and effects of adopting such arrangement for an endoscope objective optical system according to a second embodiment will be described below by using the diagrams.

Figure 1B:
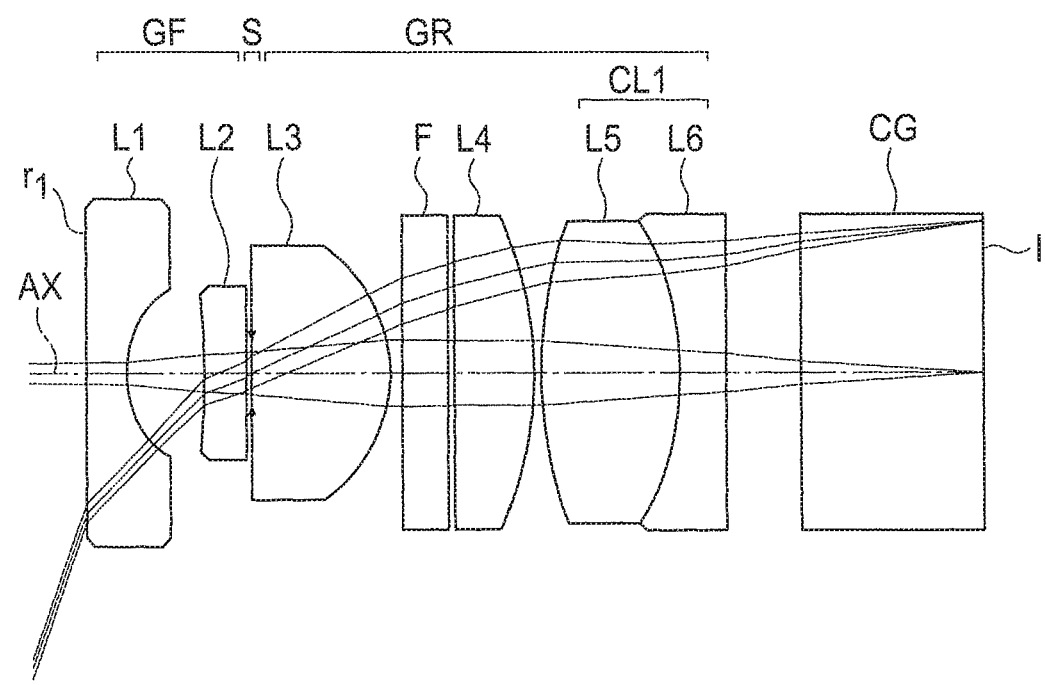
FIG. 1B is a lens cross-sectional view showing a basic arrangement of an endoscope objective optical system of a second embodiment.

FIG. 1B is a lens cross-sectional arrangement view showing an example of the basic arrangement of the endoscope objective optical system of the present embodiment.

The endoscope objective optical system of the second embodiment includes in order from an object side, a front group GF having a negative refractive power, an aperture stop S, and a rear group GR having a positive refractive power, and either the front group GF or the rear group GR includes one or more than one cemented lenses CL1, and the rear group GR includes a third lens L3 having a positive refractive power which is a single lens, on the object side, a fourth lens L4 having a positive refractive power, on the image side, and the cemented lens CL1, and the cemented lens CL1 includes a fifth lens L5 having a positive refractive power and a sixth lens L6 having a negative refractive power, and the following conditional expressions (1), (2), (3), and (4) are satisfied.

$$1.1 < Ih/ft < 1.8 \quad (1)$$

$$-ff/ft < 0.9 \quad (2)$$

$$45 < vd1 \quad (3)$$

$$LOs/Ih < 1.5 \quad (4)$$

where,

Ih denotes the maximum image height, ft denotes a focal length of an overall endoscope objective optical system, ff denotes a focal length of the front group GF, vd1 denotes Abbe's number for a glass material of the positive lens on the object side of the rear group GR, and LOs denotes a distance from a first surface r1 on the object side of the endoscope objective optical system up to the aperture stop S, and here the first surface r1 on the object side of the endoscope objective optical system is a lens surface positioned nearest to object in the endoscope objective optical system.

Moreover, in the endoscope objective optical system of the second embodiment, it is preferable that the rear group includes a fourth lens L4 having a positive refractive power which is a single lens, on the image side of the third lens L3 having a positive refractive power, on the object side, and the following conditional expression (5) is satisfied.

$$L2s/LOs < 1.7 \quad (5)$$

where,

L2s denotes a distance from the aperture stop S up to an object-side surface of the fourth lens L4 having a positive refractive power on the image side in the rear group, and LOs denotes the distance from the first surface r1 on the object side of the endoscope objective optical system up to the aperture stop S.

When an upper limit value of conditional expression (5) is exceeded, an off-axis light ray which passes through an image-side surface of the fourth lens L4 having a positive refractive power, on the image side in the rear group becomes high (becomes far from the optical axis), and a lens diameter of the fourth lens L4 having a positive refractive power becomes large. As a result, a diameter of a front-end rigid portion becomes thick, and therefore it is not preferable.

Moreover, in the endoscope objective optical system of the present invention, it is preferable that the third lens L3 having a positive refractive power, on the object side, in the rear group and the fourth lens L4 having a positive refractive power, on the image side, in the rear group satisfy the following conditional expression (6).

$$0<R1/R2<0.7 \quad (6)$$

where,

R1 denotes an image-side radius of curvature of the third lens L3 having a positive refractive power, on the object side, in the rear group GR, and R2 denotes an image-side radius of curvature of the fourth lens L4 having a positive refractive power, on the image side, in the rear group GR.

When an upper limit value of conditional expression (6) is exceeded, an on-axis lens thickness of the fourth lens L4 having a positive refractive power increases, and the overall length becomes long, and therefore it is not preferable.

In a case in which a value falls below a lower limit value of conditional expression (6), a shape of the fourth lens L4 having a positive refractive power, on the image side, becomes either (A) a planoconvex lens having a flat surface directed toward the object side, or (B) a positive meniscus lens having a convex surface directed toward the object side. Here, an effect on a coma by a lens shape in a case in which the refractive power of the lens and a glass material of the fourth lens L4 having a positive refractive power, on the image side are fixed, is to be taken into consideration.

For the lenses (A) and (B) of the shape described above, an angle of incidence of an off-axis principal light ray on the object side surface (an angle made by the principal light ray and a normal direction of the lens surface) is larger as compared to that for a lens of a shape other than the abovementioned shapes, or in other words, (C) a biconvex positive lens, or (D) a planoconvex lens having a flat surface directed toward the image side, or (E) a positive meniscus lens having a convex surface directed toward the image side. At the time of using the lenses (A) and (B), since the off-axis principal light ray is bend largely, and an off-axis coma becomes large, it is not preferable.

Significance of the arrangement and conditional expressions of the endoscope objective optical system of the second embodiment is same as the significance of the arrangement and conditional expressions of the endoscope objective optical system of the first embodiment. Therefore, repetitive description thereof is omitted.

Moreover, in the endoscope objective optical system of the first embodiment and the endoscope objective optical system of the second embodiment, it is preferable that the first lens L1 having a negative refractive power is a planoconcave lens of which an object-side surface is a flat surface.

By letting the object-side surface to be a flat surface, it is possible to reduce damage of the lens surface. Moreover, since water droplets are hard to be accumulated in a surrounding portion of the lens surface, there is no narrowing of an observable range.

Moreover, in the endoscope objective optical system of the first embodiment and the second embodiment, it is preferable that the second lens L2 having a negative refractive power is a planoconcave lens, and a concave surface thereof is directed toward the object side, and an image-side surface thereof is a flat surface.

Moreover, in the endoscope objective optical system of the first embodiment and the second embodiment, it is preferable that a refractive index of the second lens L2 having a negative refractive index is 1.75 or more.

Moreover, in the endoscope objective optical system of the first embodiment and the second embodiment, it is preferable that the third lens L3 having a positive refractive power, on the object side, is a planoconvex lens, and an object-side surface thereof is a flat surface, and an image-side surface thereof is a convex surface directed toward the image side.

Moreover, in the endoscope objective optical system of the first embodiment and the second embodiment, it is preferable that the fourth lens L4 having a positive refractive power, on the image side, is a planoconvex lens, and an object-side surface thereof is a flat surface, and an image-side surface thereof is a convex surface directed toward the image side.

Moreover, in the endoscope objective optical system of the second embodiment, it is preferable that a refractive index of the fourth lens L4 having a positive refractive power, on the image side, is higher than a refractive index of the third lens L3 having a positive refractive power, on the object side.

In the endoscope objective optical system of the present embodiment, it is preferable that a refractive index of the fifth lens L5 having a negative refractive power or the sixth lens L6 having a negative refractive index is 1.85 or more, and Abbe's number for the fifth lens L5 and the sixth lens L6 is 23 or less.

The abovementioned endoscope objective optical systems may satisfy the plurality of arrangements simultaneously. Making such arrangement is preferable for achieving a favorable endoscope objective optical system. Moreover, combinations of preferable arrangements are arbitrary. Furthermore, for each conditional expression, an upper limit value or a lower limit value of further limited numerical range of the conditional expression may be limited.

Examples will be described below. In a lens cross-sectional view of each example, a light ray when the object-side space is let to be water is described. Moreover, in each aberration diagram, a horizontal axis indicates an aberration amount. Aberration curves shown in the aberration diagrams indicate an aberration at the time of in-water observation. For the spherical aberration and the astigmatism, the unit of aberration amount is mm. Moreover, for the distortion, the unit of aberration is %. Moreover, Ih denotes the maximum image height and the unit thereof is mm, and FNO denotes an F-number. Furthermore, the unit of wavelength of aberration curve is nm.

Example 1

Figure 2A:
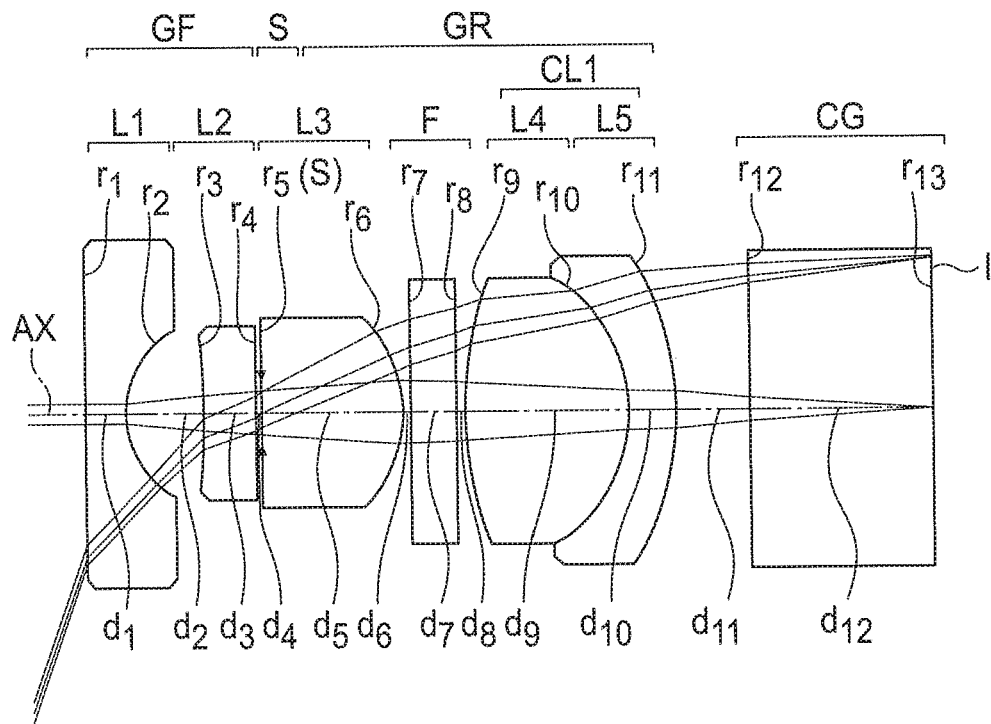
FIG. 2A is a lens cross-sectional view showing an overall basic arrangement of an endoscope objective optical system according to an example 1.
Figures 2B, 2C, 2D, 2E:
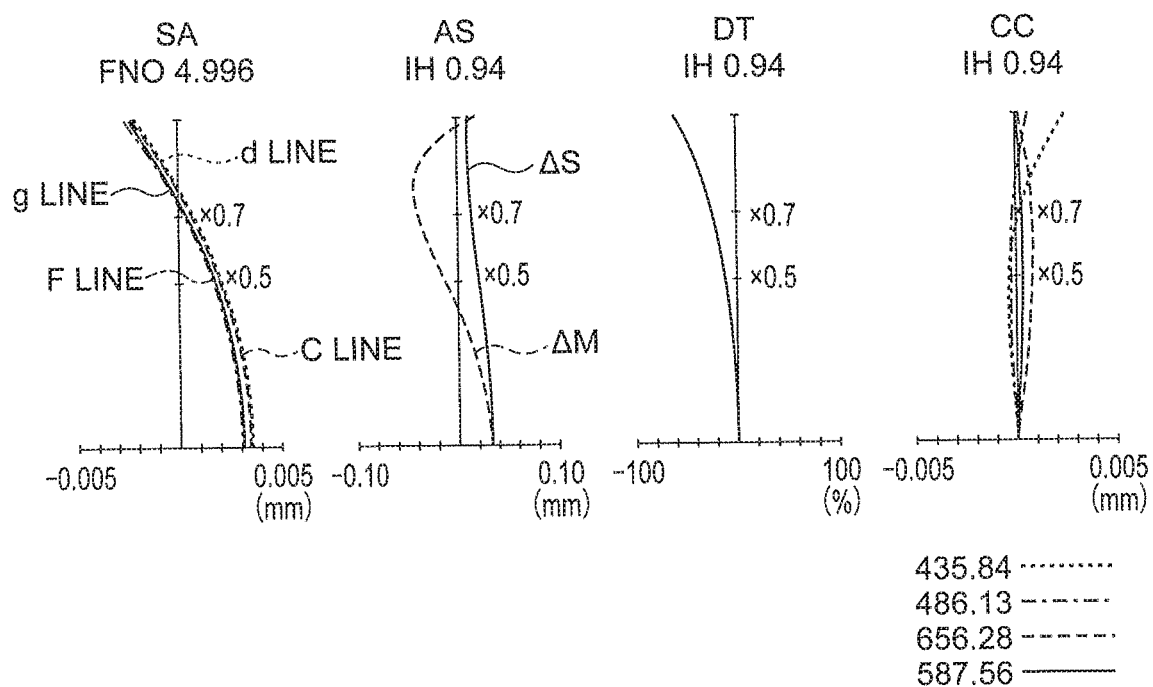
FIG. 2B, FIG. 2C, FIG. 2D, and FIG. 2E are aberration diagrams showing a spherical aberration (SA), an astigmatism (AS), a distortion (DT), and a chromatic aberration of magnification (CC) of the present example.

An endoscope objective optical system according to an example 1 will be described below. FIG. 2A is a lens cross-sectional view of the endoscope objective optical system according to the example 1. FIG. 2B shows a spherical aberration (SA), FIG. 2C shows an astigmatism (AS), FIG. 2D shows a distortion (DT), and FIG. 2E shows a chromatic aberration of magnification (CC).

The endoscope objective optical system of the example 1, as shown in FIG. 2A, includes in order from an object side, a front group GF having a negative refractive power, an aperture stop S, and a rear group GR having a positive refractive power.

The front group GF includes a first lens L1 which is a planoconcave negative lens of which an object side is a flat surface, and a second lens L2 which is planoconcave negative lens of which an image side is a flat surface.

The rear group GR includes a third lens L3 which is a planoconvex positive lens of which an object side is a flat surface, an optical filter F, a fourth lens L4 which is a biconvex positive lens, and a fifth meniscus lens L5 which is a negative lens having a convex surface directed toward an image side. Here, the fourth lens L4 which is a biconvex positive lens and the fifth meniscus lens L5 having a negative refractive power form a cemented lens CL1 having a positive refractive power.

The aperture stop S is provided to an object-side surface of the third lens L3 which is a planoconvex positive lens. The optical filter F is disposed in the rear group GR. The optical filter F is disposed between the third lens L3 which is a planoconvex positive lens and the fourth lens L4 which is a biconvex positive lens. A glass block CG is disposed on the image side of the rear group GR, assuming that a cover glass of a solid image pickup element is disposed.

A space between the cemented lens CL1 and the glass block CG is let to be a focus adjustment space, and is designed optically such that it is possible to secure an adjustment range adequately.

The example 1 is an arrangement in which there is only one single lens having a positive refractive power in the rear group GR.

In the example 1, the front group GF includes the first lens L1 having a negative refractive power and the second lens L2 having a negative refractive power. Both the first lens L1 having a negative refractive power and the second lens L2 having a negative refractive power are single lenses. In such manner, by limiting the lenses in the front group GF to be two single lenses having a negative refractive power, widening of angle and shortening of the entrance-pupil position are carried out in a space on the object side of the aperture stop S. Shortening of the entrance-pupil position is bringing the entrance-pupil position closer to the object.

When one or both of the first lens L1 having a negative refractive power and the second lens L2 having a negative refractive power is or are formed by a cemented lens, due to an increase in a lens thickness, the space on the object side of the aperture stop S becomes long. As in the present example, by letting each of the first lens L1 having a negative refractive power and the second lens L2 having a negative refractive power to be a single lens, it is possible to avoid the increase in the lens thickness in the front group GF. As a result, it is possible to minimize a space occupied by lenses in the space on the object side of the aperture stop S.

Such arrangement of the front group GF contributes to realize shortening of the length of the front group GF and to shorten the length of the overall optical system.

Next, characteristics of the first lens L1 having a negative refractive power will be described. In the first lens L1 having a negative refractive power, an object-side surface is let to be a flat surface. This structure is common as an endoscope front-end structure. In an endoscope, since illuminating light is incident directly in a case in which an object-side surface is let to be a convex surface, it is necessary to devise an idea for a light-shielding structure in an endoscope front-end portion. Therefore, in the example 1, for directly incident flare from a illumination system which is not shown in the diagram, it is not necessary to devise an idea for light-shielding in the first lens L1 having a negative refractive power and in a frame structure.

Moreover, the object side of the first lens L1 having a negative refractive power being a flat surface, there is no bulging (convex shape). Therefore, even when an object happens to hit the lens surface from the object side, a probability of the first lens L1 having a negative refractive power getting scratched is lower than that in a case of a convex surface. It is preferable to let a glass material of the first lens L1 having a negative refractive power to be sapphire which has a superior mechanical endurance. By using sapphire, a projection of a scratch on an image and an occurrence of flare due to scratch are hard to occur.

By using a glass material having a high refractive index for the second lens L2 having a negative refractive power, an absolute value of negative Petzval sum is let to be as small as possible. Moreover, in the second lens L2 having a negative refractive power, an aperture stop S side is let to be a flat surface. When such arrangement is made, in a case in which the aperture stop S is made of a thin plate, it is possible to sandwich the aperture stop S between the second lens L2 having a negative refractive power and the third lens L3 having a positive refractive power. In such manner, by letting a structure that enables to sandwich the aperture stop S in a gap between the two lenses, an air space is reduced. Reducing the air space other than the optical adjustment space contributes to shortening of the overall length of the optical system.

By using a glass material having a low refractive index for the third lens L3 having a positive refractive power, positive Petzval sum is let to be large.

The optical filter F is a filter such as a color correction filter. The color correction filter includes an absorbing material which attenuates wavelengths from a long-wavelength side of a visible range up to a near-infrared wavelength region. However, in application for urinary organs, an Nd:YAG (neodymium yttrium aluminum garnet) laser is sometimes used for the treatment of tumor. Therefore, it is desirable that a multilayer optical interference film having almost 100% reflectance with respect to a wavelength of the Nd:YAG laser is applied to one or both surfaces of the color correction filter.

Since the multilayer optical interference film has a strong dependence on angle of incidence, the reflectance varies substantially according to the angle of incidence. Therefore, in a case in which the color correction filter includes the multilayer optical interference film, it is necessary to dispose the color correction filter at a location where an angle of incidence of a principal light ray does not become excessively large. In the arrangement of the endoscope objective optical system of the example 1, it is desirable to dispose the color correction filter on the image side of the third lens L3 having a positive refractive power.

The cemented lens CL1 includes the fourth lens L4 having a positive refractive power made of a glass material having a low refractive index and the fifth meniscus lens L5 having a negative refractive power made of a glass material having a high refractive index. Moreover, the astigmatism and the coma are corrected by imparting the negative refractive power to a cemented surface. Furthermore, by letting a difference between a refractive index of an object side of the cemented surface and a refractive index of an image side of the cemented surface to be large, consideration is given to preventing a radius of curvature of the cemented surface from becoming excessively small. Accordingly, an aberration fluctuation due to decentering is suppressed. On the object side of the cemented lens CL1, there is no lens which is capable of correcting the chromatic aberration of magnification. Therefore, an ultrahigh dispersion glass is used for the fifth meniscus lens L5 having a negative refractive power in the cemented lens CL1, and the chromatic aberration of magnification is corrected collectively in the cemented lens.

Specifications of the endoscope objective optical system of the example 1 will be described below. In the endoscope objective optical system of the example 1, the maximum image height Ih in an in-water observation state is 0.942 mm. The maximum image height Ih is set by letting the maximum image height Ih to coincide with an effective image pickup area of a solid image pickup element. Therefore, in the in-water observation state, the entire effective image pickup area of the solid image pickup element is used.

Moreover, in the endoscope objective optical system of the example 1, the in-water angle of view is 139.5°. Therefore, the endoscope objective optical system of the example 1, as an endoscope objective optical system which enables the in-water observation, is an optical system with an extremely wide angle. According to the endoscope objective optical system of the example 1, it is possible to observe an object in water by using the entire effective image pickup area of the solid image pickup element.

Example 2

Figure 3A:
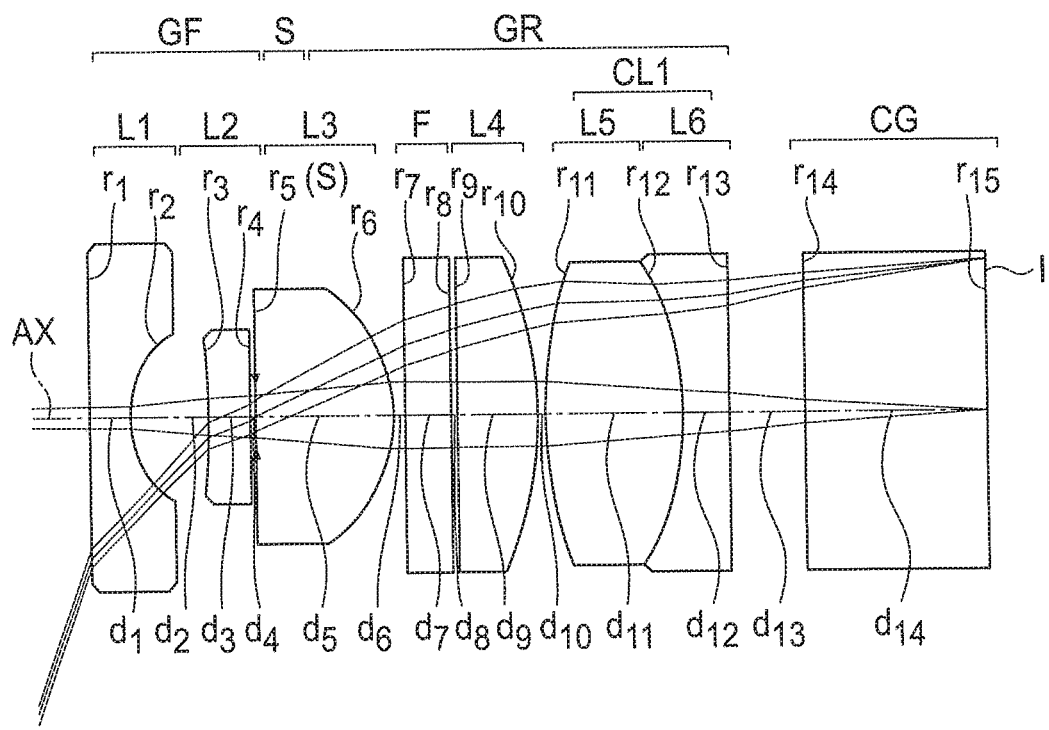
FIG. 3A is a lens cross-sectional view showing an overall basic arrangement of an endoscope objective optical system according to an example 2.
Figures 3B, 3C, 3D, 3E:
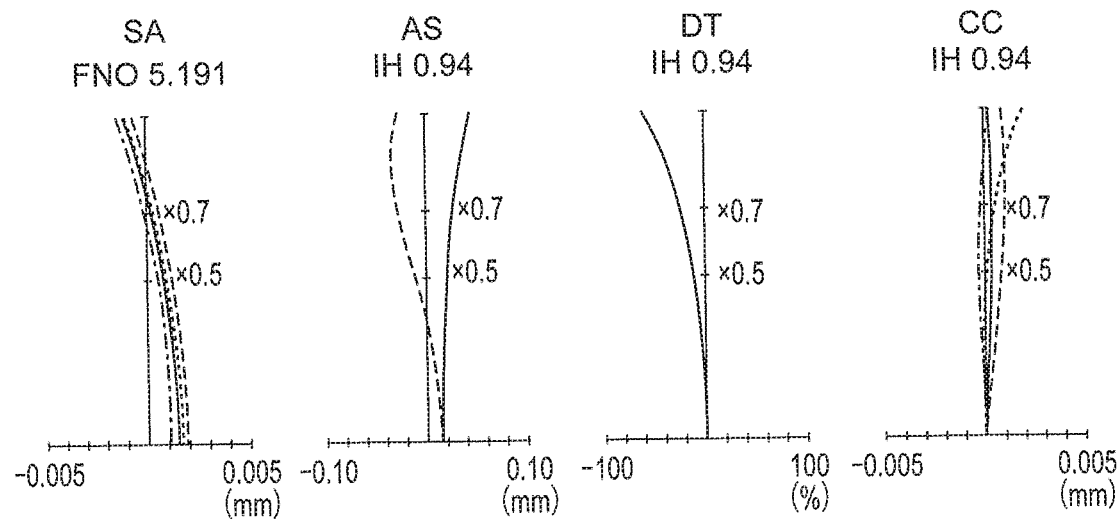
FIG. 3B, FIG. 3C, FIG. 3D, and FIG. 3E are aberration diagrams showing a spherical aberration (SA), an astigmatism (AS), a distortion (DT), and a chromatic aberration of magnification (CC) of the present example.

Next, an endoscope objective optical system according to an example 2 will be described below. FIG. 3A is a lens cross-sectional view of the endoscope objective optical system according to the example 2. FIG. 3B shows a spherical aberration (SA), FIG. 3C shows an astigmatism (AS), FIG. 3D shows a distortion (DT), and FIG. 3E shows a chromatic aberration of magnification (CC).

The endoscope objective optical system of the example 2, as shown in FIG. 3A, includes in order from an object side, a front group GF having a negative refractive power, an aperture stop S, and a rear group GR having a positive refractive power.

The front group GF includes a first lens L1 which is a planoconcave negative lens of which an object side is a flat surface, and a second lens L2 which is a planoconcave negative lens of which an image side is a flat surface.

The rear group GR includes a third lens L3 which is a planoconvex positive lens of which an object side is a flat surface, an optical filter F, a fourth lens L4 which is a planoconvex positive lens of which an object side is a flat surface, a fifth lens L5 which is a biconvex positive lens, and a sixth lens L6 which is a planoconcave negative lens of which an image side is a flat surface. Here, the fifth lens L5 which is a biconvex positive lens and the sixth lens L6 which is a planoconcave negative lens form the cemented lens CL1 having a positive refractive power.

The aperture stop S is provided to an object-side surface of the third lens L3 which is a planoconvex positive lens. The optical filter F is disposed in the rear group GR. The optical filter F is disposed between the third lens L3 which is a planoconvex positive lens and the fourth lens L4 which is planoconvex positive lens. A glass block CG is disposed on the image side of the rear group GR, assuming that a cover glass of a solid image pickup element is disposed.

A space between the cemented lens CL1 and the glass block CG is let to be a focus adjustment space, and is designed optically such that it is possible to secure an adjustment range adequately.

An arrangement of the first lens L1 having a negative refractive power and the second lens L2 having a negative refractive power in the front group GF, and the optical filter F is same as the arrangement in the example 1. Therefore, repetitive description thereof is omitted.

By using a glass material having a low refractive index for the third lens L3 having a positive refractive power, positive Petzval sum is let to be large.

The positive Petzval sum is generated even in the fourth lens L4 having a positive refractive power. However, in the fourth lens L4 having a positive refractive power, since priority is given to lowering a light-ray height than to increasing the Petzval sum, a glass material having a high refractive index is used for the fourth lens L4 having a positive refractive power. In the fourth lens L4 having a positive refractive power, the light-ray height becomes higher than that in the third lens L3 having a positive refractive power. Consequently, the on-axis lens thickness and the refractive power of the image-side surface of the fourth lens L4 having a positive refractive power have an effect on an outer diameter from the fourth lens L4 onward.

In the fourth lens L4 having a positive refractive power, as the refractive index is made higher, the radius of curvature increases accordingly. With the increase in the radius of curvature, it is possible to make the on-axis lens thickness thin. Furthermore, an effect of reduction of an air conversion length is also achieved.

The cemented lens CL1 includes the fifth lens L5 having a positive refractive power made of a glass material having a low refractive index and the sixth meniscus lens L6 having a negative refractive power made of a glass material having a high refractive index. Moreover, the astigmatism and the coma are corrected by imparting the negative refractive power to a cemented surface. Furthermore, by letting a difference between a refractive index of an object side of the cemented surface and a refractive index of an image side of the cemented surface to be large, consideration is given to preventing a radius of curvature of the cemented lens from becoming excessively small. Accordingly, an aberration fluctuation due to decentering is suppressed. On the object side of the cemented lens CL1, there is no lens which is capable of correcting the chromatic aberration of magnification. Therefore, an ultrahigh dispersion glass is used for the sixth lens L6 having a negative refractive power in the cemented lens CL1, and the chromatic aberration is corrected collectively in the cemented lens.

Specifications of the endoscope objective optical system of the example 2 will be described below. In the endoscope objective optical system of the example 1, the maximum image height Ih in the in-water observation state is 0.942 mm. The maximum image height Ih is set by letting the maximum image height Ih to coincide with an effective image pickup area of the solid image pickup element. Therefore, in the in-water observation state, the entire effective image pickup area of the solid image pickup element is used.

Moreover, in the endoscope objective optical system of the example 2, the in-water angle of view is 138.4°. Therefore, the endoscope objective optical system of the example 2, as an endoscope objective optical system which enables the in-water observation, is an optical system with an extremely wide angle. According to the endoscope objective optical system of the example 2, it is possible to observe an object in water by using the entire effective image pickup area of the solid image pickup element.

Example 3

Figure 4A:
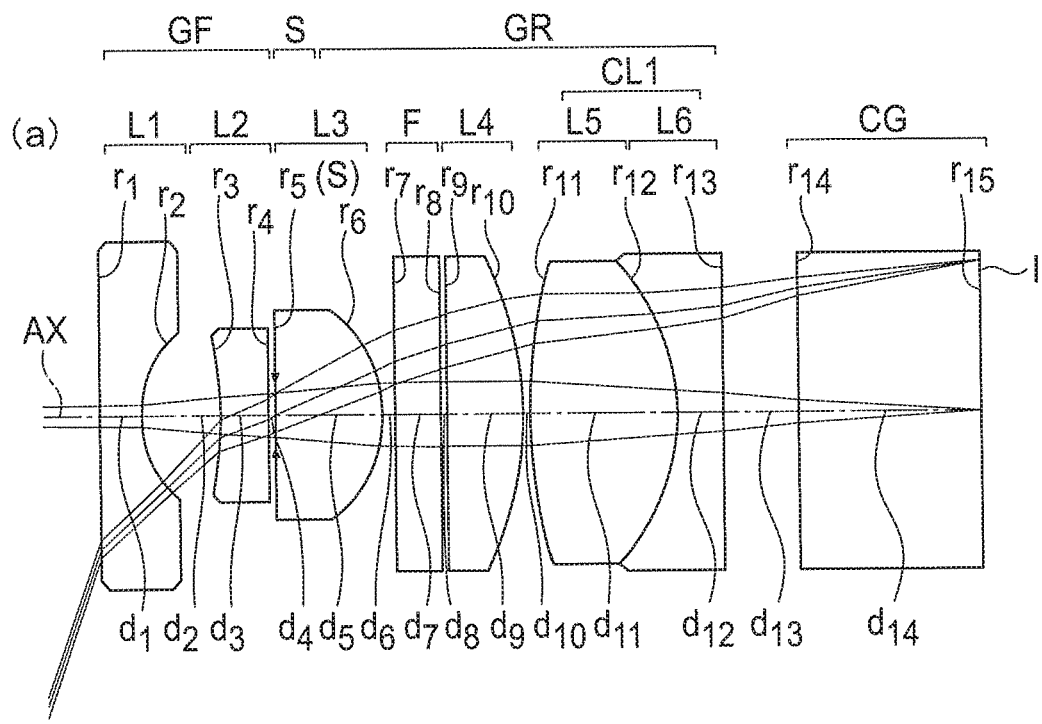
FIG. 4A is a lens cross-sectional view showing an overall basic arrangement of an endoscope objective optical system according to an example 3.
Figures 4B, 4C, 4D, 4E:
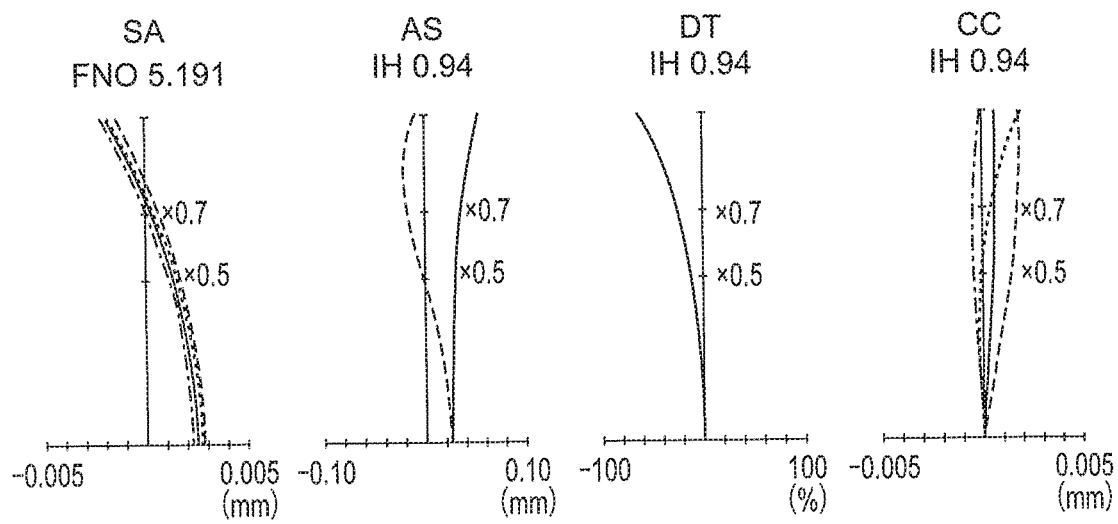
FIG. 4B, FIG. 4C, FIG. 4D, and FIG. 4E are aberration diagrams showing a spherical aberration (SA), an astigmatism (AS), a distortion (DT), and a chromatic aberration of magnification (CC) of the present example.

An endoscope objective optical system according to an example 3 will be described below. FIG. 4A is a lens cross-sectional view of the endoscope objective optical system according to the example 3. FIG. 4B shows a spherical aberration (SA), FIG. 4C shows an astigmatism (AS), FIG. 4D shows a distortion (DT), and FIG. 4E shows a chromatic aberration of magnification (CC).

The endoscope objective optical system of the example 3, as shown in FIG. 4A, includes in order from an object side, a front group GF having a negative refractive power, an aperture stop S, and a rear group GR having a positive refractive power.

The front group GF includes a first lens L1 which is a planoconcave negative lens of which an object side is a flat surface, and a second lens L2 which is a planoconcave negative lens of which an image side is a flat surface.

The rear group GR includes a third lens L3 which is a planoconvex positive lens of which an object side is a flat surface, an optical filter F, a fourth lens L4 which is a planoconvex positive lens of which an object side is a flat surface, a fifth lens L5 which is a biconvex positive lens, and a sixth lens L6 which is a planoconcave negative lens of which an image side is a flat surface. Here, the fifth lens L5 which is a biconvex positive lens and the sixth lens L6 which is a planoconcave negative lens form a cemented lens CL1 having a positive refractive power.

The aperture stop S is provided to an object-side surface of the third lens L3 which is a planoconvex positive lens. The optical filter F is disposed in the rear group GR. The optical filter F is disposed between the third lens L3 which is a planoconvex positive lens and the fourth lens L4 which is a planoconvex positive lens. A glass block CG is disposed on the image side of the rear group GR, assuming that a cover glass of a solid image pickup element is disposed.

A space between the cemented lens CL1 and the glass block CG is let to be a focus adjustment space, and is designed optically such that it is possible to secure an adjustment range adequately.

In the example 3, an optical glass other than sapphire is used as a glass material of the first lens L1 having a negative refractive power. Although the mechanical endurance of the optical glass used is inferior to that of sapphire, workability is superior to that of sapphire. Due to price of the glass material and advantage of ease of processing, it is possible to manufacture at a low cost compared to a case in which sapphire is used.

Specifications of the endoscope objective optical system of the example 3 will be described below. In the endoscope objective optical system of the example 3, the maximum image height Ih in the in-water observation state is 0.942 mm. The maximum image height Ih is set by letting the maximum image height Ih to coincide with an effective image pickup area of the solid image pickup element. Therefore, in the in-water observation state, the entire effective image pickup area of the solid image pickup element is used.

Moreover, in the endoscope objective optical system of the example 3, the in-water angle of view is 137.3°. Therefore, the endoscope objective optical system of the example 3, as an endoscope objective optical system which enables the in-water observation, is an optical system with an extremely wide angle. According to the endoscope objective optical system of the example 3, it is possible to observe an object in water by using the entire effective image pickup area of the solid image pickup element.

Numerical data of each example is shown below. Regarding symbols, r denotes a radius of curvature of each surface, d denotes a thickness of each optical member or an air space, nd denotes a refractive index for a d-line of each optical member, vd denotes Abbe's number for the d-line for each optical member, Ih denotes the maximum image height, ft denotes a focal length of the overall endoscope objective optical system, ff denotes a focal length of the front group of the endoscope objective optical system, LOs denotes a distance from the first surface r1 on the object side up to the aperture stop (stop), L2s denotes a distance from the aperture stop S up to an object-side surface of the positive lens on the image side in the rear group, FNO denotes an F-number, and co denotes a half angle of view. Each of Ih and ω is for observation assuming that the observation is in-water observation. Moreover, the unit of r, d, ft, LOs, and L2s is mm. The unit of ω is ° (degrees).

Example 1

Unit mm

Surface data

| Surface no. | r | d | nd | vd |
|---|---|---|---|---|
| 1 | ∞ | 0.25 | 1.76820 | 71.79 |
| 2 | 0.600 | 0.50 | 1 | — |
| 3 | −5.480 | 0.34 | 2.00330 | 28.27 |
| 4(Stop) | ∞ | 0.03 | 1 | — |
| 5 | ∞ | 0.91 | 1.64000 | 60.08 |
| 6 | −0.836 | 0.05 | 1 | — |
| 7 | ∞ | 0.30 | 1.52100 | 65.13 |
| 8 | ∞ | 0.05 | 1 | — |
| 9 | 2.248 | 1.05 | 1.57099 | 50.80 |
| 10 | −0.970 | 0.30 | 1.95906 | 17.47 |
| 11 | −1.890 | 0.47 | 1 | — |
| 12 | ∞ | 1.19 | 1.51633 | 64.14 |
| Image pickup surface | ∞ | | | |

Various data

| | |
|---|---|
| Ih | 0.942 |
| ft | 0.703 |
| ff | −0.630 |
| LOs | 1.090 |
| FNO | 4.996 |
| 2ω | 139.5 |

Example 2

Unit mm

Surface data

| Surface no. | r | d | nd | vd |
|---|---|---|---|---|
| 1 | ∞ | 0.25 | 1.76820 | 71.79 |
| 2 | 0.639 | 0.51 | 1 | — |
| 3 | −3.127 | 0.27 | 2.00330 | 28.27 |
| 4(Stop) | ∞ | 0.03 | 1 | — |
| 5 | ∞ | 0.89 | 1.58913 | 61.14 |
| 6 | −0.961 | 0.08 | 1 | — |
| 7 | ∞ | 0.30 | 1.52100 | 65.13 |
| 8 | ∞ | 0.03 | 1 | — |
| 9 | ∞ | 0.51 | 1.88300 | 40.76 |
| 10 | −2.500 | 0.05 | 1 | — |
| 11 | 2.665 | 0.89 | 1.63854 | 55.38 |
| 12 | −1.817 | 0.30 | 1.95906 | 17.47 |
| 13 | ∞ | 0.47 | 1 | — |
| 14 | ∞ | 1.19 | 1.51633 | 64.14 |
| Image pickup surface | ∞ | | | |

Various data

| | |
|---|---|
| Ih | 0.942 |
| ft | 0.725 |

-continued

Unit mm

| | |
|---|---|
| ff | −0.579 |
| L0s | 1.030 |
| L2s | 1.300 |
| FNO | 5.191 |
| 2ω | 138.4 |

Example 3

Unit mm

Surface data

| Surface no. | r | d | nd | vd |
|---|---|---|---|---|
| 1 | ∞ | 0.27 | 1.88300 | 40.76 |
| 2 | 0.703 | 0.51 | 1 | — |
| 3 | −2.186 | 0.31 | 1.88300 | 40.76 |
| 4(Stop) | ∞ | 0.03 | 1 | — |
| 5 | ∞ | 0.69 | 1.56384 | 60.67 |
| 6 | −0.832 | 0.08 | 1 | — |
| 7 | ∞ | 0.30 | 1.52100 | 65.13 |
| 8 | ∞ | 0.03 | 1 | — |
| 9 | ∞ | 0.50 | 1.85026 | 32.27 |
| 10 | −2.194 | 0.05 | 1 | — |
| 11 | 3.597 | 0.94 | 1.72916 | 54.68 |
| 12 | −1.356 | 0.30 | 1.95906 | 17.47 |
| 13 | ∞ | 0.47 | 1 | — |
| 14 | ∞ | 1.19 | 1.51633 | 64.14 |
| Image pickup surface | ∞ | | | |

Various data

| | |
|---|---|
| Ih | 0.942 |
| ft | 0.725 |
| ff | −0.518 |
| L0s | 1.088 |
| L2s | 1.101 |
| FNO | 5.189 |
| 2ω | 140.4 |

Corresponding values of the conditional expression are shown below. Conditional Expression Example1 Example2 Example3

| Conditional Expressions | Example1 | Example2 | Example3 |
|---|---|---|---|
| (1) Ih/ft | 1.339 | 1.299 | 1.299 |
| (2) −ff/ft | 0.896 | 0.798 | 0.714 |
| (3) vd1 | 60.08 | 61.14 | 60.67 |
| (4) L0s/Ih | 1.157 | 1.093 | 1.155 |
| (5) L2s/L0s | — | 1.262 | 1.012 |
| (6) R1/R2 | | | |

Various embodiments of the present invention have been described heretofore. However, the present invention is not restricted to the embodiments described heretofore, and embodiments in which the arrangements of the embodiments are combined appropriately without departing from the scope of the invention also fall in the category of the present invention.

As described heretofore, the present invention is useful for an endoscope objective optical system which has a small diameter, a wide in-water angle of view, a favorable correction of the chromatic aberration, and a short overall length of the optical system.

According to the present invention, it is possible to provide an endoscope objective optical system which has a small diameter, a wide in-water angle of view, a favorable correction of the chromatic aberration, and a short overall length of the optical system.

What is claimed is:

1. An endoscope objective optical system, consisting of, in order from an object side:
   a front group having a negative refractive power;
   an aperture stop; and
   a rear group having a positive refractive power, wherein one of the front group and the rear group includes not less than one cemented lens, and
   the cemented lens includes a lens having a positive refractive power and a lens having a negative refractive power, and
   the rear group includes a first single lens having a positive refractive power on the object side, and
   the following conditional expressions (1), (2), (3), and (4) are satisfied:

$$1.1 < Ih/ft < 1.8 \tag{1}$$

$$-ff/ft < 0.9 \tag{2}$$

$$45 < vd1 \tag{3}$$

$$L0s/Ih < 1.5 \tag{4}$$

where,
Ih denotes the maximum image height in an in-water observation state,
ft denotes a focal length of an overall endoscope objective optical system,
ff denotes a focal length of the front group,
vd1 denotes Abbe's number for a glass material of the positive lens on the object side of the rear group, and
L0s denotes a distance from a first surface on the object side of the endoscope objective optical system up to the aperture stop, and here
the first surface on the object side of the endoscope objective optical system is a lens surface positioned nearest to an object in the endoscope objective optical system.

2. The endoscope objective optical system according to claim 1, wherein the rear group includes a second single lens having a positive refractive power on an image side of the lens having a positive refractive power on the object side, and the following conditional expression (5) is satisfied:

$$L2s/L0s < 1.7 \tag{5}$$

where,
L2s is a distance from the aperture stop up to an object-side surface of the lens having a positive refractive power on the image side in the rear group, and
L0s denotes the distance from the first surface on the object side of the endoscope objective optical system up to the aperture stop.

3. The endoscope objective optical system according to claim 2, wherein the lens having a positive refractive power, on the object side, in the rear group and the lens having a positive refractive power, on the image side, in the rear group satisfy the following conditional expression (6):

$$0 < R1/R2 < 0.7 \tag{6}$$

where,
R1 denotes an image-side radius of curvature of the lens having a positive refractive power, on the object side, in the rear group, and R2 denotes an image-side radius of curvature of the lens having a positive refractive power, on the image side, in the rear group.

4. The endoscope objective optical system according to claim 1, wherein the front group includes in order from the object side, a first negative lens and a second negative lens, and the second negative lens has a concave surface on the object side.

5. The endoscope objective optical system according to claim 1, wherein the endoscope objective optical system enables the in-water observation and an observation in air.

* * * * *